(12) United States Patent
Hoegemeyer

(10) Patent No.: US 6,875,905 B2
(45) Date of Patent: Apr. 5, 2005

(54) METHOD OF PRODUCING FIELD CORN SEED AND PLANTS

(75) Inventor: Thomas C. Hoegemeyer, Hooper, NE (US)

(73) Assignee: Cerrado Natural Systems Group, Inc., Hooper, NE (US)

(*) Notice: Subject to any disclaimer, the term of this patent is extended or adjusted under 35 U.S.C. 154(b) by 0 days.

(21) Appl. No.: 09/998,664

(22) Filed: Dec. 3, 2001

(65) Prior Publication Data

US 2002/0104115 A1 Aug. 1, 2002

Related U.S. Application Data

(60) Provisional application No. 60/251,127, filed on Dec. 4, 2000.

(51) Int. Cl.$^7$ ............................. A01H 1/02; A01H 1/00; A01H 5/00; A01H 5/10
(52) U.S. Cl. ...................... 800/275; 800/271; 800/274; 800/320.1
(58) Field of Search .................................. 800/271, 274, 800/275, 320.1, 260, 266, 273, 320; 435/424

(56) References Cited

U.S. PATENT DOCUMENTS

| | | | |
|---|---|---|---|
| 5,304,717 A | | 4/1994 | Miller |
| 5,491,294 A | * | 2/1996 | Miller ........................ 800/200 |
| 6,040,507 A | | 3/2000 | Hoegemeyer |

OTHER PUBLICATIONS

Kermicle et al. Maydica 35(4): 399–408, 1990.*
Podol'skaya, A. Sov. Genet. (English translation) 17(10) : 1197–1202, 1982.*
Nelson, O.E. The Maize Handbook, Freeling et al, eds, Springer–Verlag: New York, pp. 496–503, 1994*
Sevov et al. Genet. Selek. 12(1):21–25, 1979.*
Podol'skaya, A. Genetika 24(8): 1427–1431, 1988.*
North Carolina Agric Res Serv: "Maize DB is a public internet gateway– Notice of Release of NC344, NC 346, NC348, NC350, NC352, and NC354 Maize Breeding Lines" Germplasm Release Notice. Retrieved from http://www.a-gron.missouri.edu/cgi–bin/sybgw mdb/mdb3/reference/248185 XP002231720. United States.
Nelson Oliver E. : "The Gametophyte Factors of Maize." The Maize Handbook., 1994, pp. 496–503, XP008013956, Springer–Verlag New York, Inc. ; Springer–Verlag 175 Fifth Avenue, New York, Bew York 10010, USA; Heidelberger Platz 3, D–1000 Berlin, Germany. pp. 499–502. United States.
Kermicle J. L. et al. : "Cross–Incompatibility Between Maize and Teosinite" Maydica, Istituto Sperimentale Per La Cerealicoltura, Bergamo, IT, vol. 35, No. 4, Jun. 19, 1990, pp. 399–408, XP001031166, ISSN: 0025–6153. United States.
Podol, Skaya A.. P: "Introduction of Gametophyte Gene GA1 into the Genotype of High–Lysine Maize" Genetika, vol. 24, No. 8, 1988, pp. 1427–1431, XP008013884, ISSN 0016–6758. The whole document. USSR.
Sevov A. Et AL: "Use of the GA–S Gene as a genetic Barrier of Noncrossability Between Normal and High Lysine Maize" Genetika I Selektsiya, vol. 12, No. 1, 1979, pp. 21–25, XP002231718, ISSN: 0016–6758. The whole document. USSR.
Shmaraev Et AL: "Hybridization of Maize with Teosinite" CAB, XP002181801. The whole document. USSR.
Whitely, J.R., Thomas W. I., & Johnson I. J., "Cross–Incompatibility in Maize" Agronomy Journal, Journal Paper No. J–3152 of the Iowa Agr. Exp. Sta., Ames, Iowa. Project 345. Mar. 6, 1957. pp. 513–518. United States.
Thomas Walter I. "Transferring the GA–S Factor for Dent–Incompatibility to Dent–Compatible Lines of Popcorn" Contribution from the Agronomy Department, Iowa Agr. Exp. Sta., Ames, Iowa. Project 345. Approved for publication as Journal Pater J–2742. Apr. 7, 1955. United States.
Nelson Oliver E. "Non–Reciprocal Cross–Sterility in Maize" Purdue University Agricultural Experiment Station, Lafayette, Indiana. 1951, Published as Journal Paper No. 544, pp. 101–124. United States.

* cited by examiner

Primary Examiner—David T. Fox
(74) Attorney, Agent, or Firm—Jondle & Associates P.C.

(57) ABSTRACT

This invention relates to yellow field corn inbreds and hybrids. More specifically, the invention relates to methods of producing inbreds and hybrid plants and to methods of producing corn seed which restricts the amount of foreign pollen cross pollination.

15 Claims, No Drawings

METHOD OF PRODUCING FIELD CORN SEED AND PLANTS

BACKGROUND OF THE INVENTION

The present invention relates to methods of producing field corn seed which limits outside or foreign pollen from nearby fields from fertilizing and contaminating the seed produced. In the last several years there has been concern in the grain handling industry about the ability to export corn from the U.S. Some companies, particularly in Europe, have expressed a concern that consumers may prefer grain produced without commingling of GMO (genetically modified organism) grain. Non-GMO grain is produced from traditional varieties and does not contain genes which have been introduced from other organisms via biotechnology. Since corn pollen can travel several miles and still be viable, unrealistically large isolation distances of non-GMO production fields would be required to produce corn free of contamination by GMO corn pollen. It also became apparent that: a) advanced DNA analysis techniques, such as PCR, are able to detect GMO's in food at extremely low levels, and b) it is difficult to get different countries and food companies to agree to a tolerance level higher than zero.

For decades, popcorn seed production in the corn belt area being contaminated by dent pollen has been a serious problem even with proper isolation distances. A small percentage of dent corn pollen contamination often occurs in popcorn seed fields grown under ideal conditions. This requires extra expense to separate popcorn by dent hybrid ears from the commercial crop.

Some varieties of popcorn will not set seed when pollinated by any field corn or certain other varieties of popcorn, but no difficulty is experienced in making the reciprocal cross. The genetic basic of this non-reciprocal cross-incompatibility is a multiple allelic series at the ga locus on the fourth chromosome such that $Ga^s/Ga^s$ plants will not set seed with ga (field corn) pollen but will set seed with $Ga_1^s$ or $Ga_1$ pollen. Plants which are ga/ga will set with ga, or $Ga^s$ pollen. When both ga and $Ga^s$ pollen-tubes are competing in $ga/Ga^s$ styles, only the $Ga^s$ gametes effect fertilization. The cross-sterile allele $Ga^s$, also called GaS or $Ga_1^s$, is found both in the popcorns of commercial importance in this country and in South American popcorns.

Gametophytic alleles are comparable to the self-sterility genes found in strictly cross-fertilized plants such as Nicotiana, Oenothera, Trifolium, etc., in that there is interaction between the stylar tissue and the male gametophyte. When the female parent is homozygous recessive $ga_1$, $ga_1$ pollen can compete successfully against $Ga_1$ and fertilize half of the ovules. However, if the plant used as the egg parent is heterozygous or homozygous $Ga_1$, the $ga_1$ pollen is a poor competitor and achieves fertilization in only 0–4% of the ovules. In the absence of competition, that is, if only $ga_1$ pollen is used in the cross, full seed set is obtained regardless of the genotype of the female parent. Thus the incompatibility between $ga_1$ pollen and $Ga_1$ silk is not detectable in the absence of competing $Ga_1$ pollen. One allele was designated $Ga_1^s$ since its effect is stronger than $Ga_1$.

The most important difference between what has been called $Ga_1$ and $Ga_1^s$ (also identified herein as $Ga^s$ or GaS) is that $ga_1$ pollen completely fails to function on styles homozygous for $Ga_1^s$ even in the absence of competing pollen. Crosses of $ga_1$ pollen on styles heterozygous for $Ga_1^s$ yield a partial seed set. Less seed is set when the female parent is heterozygous $Ga_1^s Ga_1$ than when a heterozygous $Ga_1^s ga_1$ plant is used. The total amount of seed produced in such crosses varies greatly from plant to plant. Also, $Ga_1^s$ may be the same as Ga plus one or more modifier genes.

While the GaS allele has been found in certain popcorns and in some exotic Central American maize population, in popcorns, the gene is also linked and otherwise associated with genes conditioning special starch characteristics, poor roots and stalks, and unacceptable levels of performance, particularly for yield. Also, efforts in converting white corn inbreds to the GaS allele (from popcorn) have resulted in lines which tended to be poorer than the original lines. Presently, this white corn material is obsolete, and its performance level is seriously deficient, particularly in root strength and yield level. In exotic corn germplasm, use of the GaS allele is made difficult due to its association with poor roots and stalks, day length sensitivity, and these exotics—as well as their derived breeding lines—are generally grossly unadapted to the US Cornbelt. The GaS gene has not been commercially used in field yellow dent or yellow flint corn due in part to: 1) the yield drag and the agronomic performance problems associated with moving the GaS gene into dent corn from popcorn or exotic maize or white corn; and 2) the difficulty in making crosses, e.g., A×B may set seed, while the reciprocal cross is sterile.

A contamination problem arose in mid-September, 2000 when a GMO corn variety, StarLink, was found to have been used in several food products. It had been approved by the EPA, USDA, and FDA for feed purposes only, and not for human food purposes. StarLink corn was found commingled in much of the U.S. corn supply. Analyzing samples from trucks, in elevators, in storage bins, and in shipments to food processors was both difficult and expensive. Quick tests using enzyme-linked immunoassay are available but they have limits of detection of about half of one percent, and they cost several dollars per sample. A much more accurate testing system is available, using PCR, however, it costs several hundred dollars and typically takes several days.

Most of the European countries have effectively put a ban on approval of grain that contains even a very low percentage of GMO contamination. Japan and Korea are in the process of defining which GMO's they will accept and which food uses they will insist on using identity-preserved non-GMO grains. Currently, U.S. baby food makers Heinz and Gerber will only use non-GMO grains. The current corn inbreds and hybrids and methods are not successful in preventing pollen contamination in cross-pollinated crops. U.S. biotech companies release, and farmers are continuing to grow, non-approved GMO varieties. This has resulted in a loss of export markets for U.S. grains. A reliable method to prevent unwanted outside GMO pollen from pollinating either a production field and/or a grower's field is needed to assist in producing non-GMO corn.

SUMMARY OF THE INVENTION

The invention provides for method of producing hybrid $F_1$ corn seed and subsequent $F_2$ seed and grain which are either: 1) free of contamination or pollination from any outside pollen sources, such as nearby corn fields or 2) have a dramatically reduced amount of pollination from any outside pollen source.

In one preferred embodiment, the hybrid and $F_2$ seed production methods herein use parental inbreds which are homozygous for the dominant GaS allele. In another embodiment of the present invention, one or more parental lines are heterozygous for the dominant GaS allele. The corn parental lines used are preferably elite inbred lines.

The present invention also provides for methods of producing elite inbred lines and hybrids which are homozygous or heterozygous for the GaS allele.

Definitions

In the description and tables which follow, a number of terms are used. In order to provide a clear and consistent understanding of the specification and claims, including the scope to be given such terms, the following definitions are provided:

Allele. Allele is any of one or more alternative forms of a gene, all of which alleles relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotypes of the $F_1$ hybrid.

Commercial hybrid. A yellow corn hybrid that has been sold commercially to farmers.

Cross-fertile. Cross-fertile refers to the ability of one plant genotype to accept pollen from a plant of another genotype, and results in seeds being produced.

Cross-incompatibility. Cross-incompatibility refers to the inability of a plant genotype to be fertilized by pollen from a plant of another genotype, even though the first plant is fertile when pollinated by its own pollen.

Elite yellow corn inbred. An elite yellow corn inbred refers to a yellow dent or flint corn inbred plant which is a parent of a commercial grown hybrid.

Elite yellow corn hybrid. An elite yellow corn hybrid refers to a yellow dent or flint corn hybrid plant which is commercially sold to farmers.

Field corn. Field corn refers to corn plants which are commercially grown in a farmer's field and which produce yellow dent or flint corn grain.

Foreign GMO pollen. Foreign GMO pollen refers to any pollen produced from plants in a nearby or adjacent planting of GMO plants, which outcrosses with corn plants in adjacent fields.

GaS. As used herein, GaS is a dominant cross-incompatibility allele. GaS has one or more associated modifier alleles on chromosome 4 of corn for the cross-incompatibility characteristic. GaS also has been previously designated as $Ga_1$ and $Ga_1^s$.

GaS modifier allele(s). GaS modifier allele(s) include one or more alleles at one or more loci on chromosome 4 of corn and which affect the expression of the GaS allele.

Genetically modified organism (GMO). Genetically modified organism or GMO refers to a plant or plant cells having one or more transgenes. Examples include Bt corn and Roundup® herbicide resistant corn.

Heterozygous. Heterozygous means a genetic condition existing when different alleles reside at corresponding loci on homologous chromosomes.

Homozygous. Homozygous means a genetic condition existing when identical alleles reside at corresponding loci on homologous chromosomes.

Outcrossing. Outcrossing refers to cross-pollinations with a plant differing in genetic constitution.

Plant. As used herein, the term "plant" includes plant cells, plant protoplasts, plant cell tissue cultures from which maize plants can be regenerated, plant calli, plant clumps and plant cells that are intact in plants, or parts of plants, such as embryos, pollen, ovules, flowers, kernels, ears, cobs, leaves, seeds, husks, stalks, roots, root tips, anthers, silk and the like.

DETAILED DESCRIPTION OF THE INVENTION

The present invention uses a non-reciprocal cross sterility system to prevent corn (*Zea mays*) plants from being pollinated by stray pollen and locks in or locks out recombinant DNA and the associated proteins. The present invention specifically addresses DNA and the associated proteins resulting from stray pollen from "Genetically Modified Organisms" (GMO's). The present invention also produces "stray pollen protected" maize hybrids, which means that the hybrid plant containing this gene system accepts only pollen from corn plants with the $Ga_1^s$ genotype and are not fertilized by corn pollen that originates from neighboring yellow dent hybrids that may or may not contain transgenes.

Corn endosperm results from the fertilization by one of the generative nuclei of the antipodal cells in the embryo sac. However, the bulk of the protein and the bulk of the DNA present in the zygote result from the fertilization of the egg nucleus by the other generative nucleus. The present invention involves protecting both the endosperm as well as the germ tissue of the kernel from contamination by DNA of undesired pollen sources. This in turn prevents the replication of the contaminant DNA and translation into contaminant proteins. Therefore the method of the present invention results in the production of maize kernels on such plants that are free of the foreign DNA and associated expressed proteins that are objectionable for certain segments of the grain trade.

In one preferred embodiment, the method of the present invention is used to prevent Yieldgard™, Naturegard™, and RoundUp Ready™ corn (GMO corn examples) from crossing with maize carrying the genotype GaS/GaS. All U.S. cornbelt dent maize GMO hybrids containing these and any other biotech traits are incapable of crossing with the lines and hybrids of the present invention, thereby eliminating concerns about foreign pollination from corn plants having one or more GMOs. The use of the elite corn inbreds of the present invention having cross-incompatibility allele GaS has important applications in both seed production and commercial production of corn hybrids. A serious problem in the production of hybrid corn seed is contamination by corn pollen from nearby corn fields having one or more biotech genes such as Bt or RoundUp Ready™. This situation arises because GMO corn inbreds and hybrids are perfectly fertile with all field corn pollen.

In the instant invention the factor for cross-incompatibility GaS, along with one or more GaS modifier genes is transferred into elite inbreds, thus insuring in a production field that the female plants would set seed only with pollen from the male rows in the same field and not allow cross pollination with any dent pollen which should happen to drift into the field from nearby fields. Through all stages of seed production and commercial production, these cross-sterile types are incapable of setting seed with drifting field corn pollen. With the number of hybrids having biotech genes, and the difficulty of isolating seed production fields of such hybrids from others which are a source of contaminating pollen, the method of the present invention achieves genetic isolation from transgenic corn contaminants.

In another preferred embodiment of the present invention, the germplasm source of GaS allele is crossed to one or more elite corn inbreds, hybrids, or populations. The $F_1$'s are backcrossed to their respective elite lines to obtain $BC_1$, $BC_2$, $BC_3$, $BC_4$, $BC_5$, $BC_6$ and $BC_7$ lines. These BC populations are then available for further selection. For example, $BC_5$ lines are selfed and selected for homozygosity. These $BC_5$ selfed lines are then crossed with various elite tester lines to produce hybrids for commercial testing.

The present invention can be used to grow certified GMO-free maize for specific food uses and exports as required. Again, this requires the use of homozygous (GaS GaS) hybrids which will reject all non-GaS pollen.

In another embodiment of the invention, the heterozygous state (GaS ga) is present in a corn hybrid to drastically reduce off-type pollen contamination in hybrids. Pollen that has the recessive ga allele, carried by all known cornbelt yellow dent maize, does not compete with GaS pollen on the silks of heterozygotes. As long as there is sufficient pollen around, the amount of blown-in pollen contamination will be drastically reduced. There is about 10 to 100 times reduction in off-type contamination when using the heterozygous GaS/ga hybrids in the present invention.

Another use of the present invention is in refuge areas around insect-protected biotech maize (Bt corn). Refuge areas are required by USDA and EPA. If a farmer chose to segregate the grain he could still identity preserve the non-GMO grain from his refuge area.

Other uses for the method and products of the present invention include: 1) developing premium-branded food corns for both white and yellow varieties, soft and hard textures for many different milling uses, as well as specialty starch, protein and oil types; 2) producing pharmaceutical proteins to dramatically improve purity where isolation alone will never keep out all pollen contamination; 3) using combinations of GaS plus recessive genes (such as waxy, white, white-cap, etc.) as a built-in quality control method for assaying purity which eliminates need for expensive DNA testing; 4) using the GaS allele to create DNA constructs to insert into the corn genome to link with certain traits that you want to control transmission of, e.g., male sterility. Traits could appear in male parent plants, but not the offspring. A construct is made having GaS allele and a male sterility gene. This construct is then backcrossed into a "female" inbred. Then the cross GaS-ms/GaS-ms is crossed as a female with pollen of a plant of GaS-ms/ga-+ yields all sterile progeny, suitable for use as a female in a seed field without detasseling, and the $F_1$ hybrid is all fertile; and 5) the GaS gene system could be transformed into other crop species and perform the same function.

EXAMPLES

The following examples are provided to further illustrate the present invention and are not intended to limit the invention beyond the limitations set forth in the appended claims.

Example 1

Exotic Germplasm Source of GaS and Initial Crosses to Elite Germplasm

Research was conducted on several sterility systems, both natural and transgenetic (GMO), for use in seed production. During the 1998–1999 winter, seed of several Ga genetic stocks were acquired as unadapted exotic germplasm releases from North Carolina State University. This seed was planted in a breeding nursery near Hooper, Nebr. in the spring of 1999. Crosses were made between these germplasm lines and several elite lines, including: LH185-waxy (LH185wx) was crossed with NC346; HX622 crossed with NC344; and LH198-waxy, HX734, HX844, A681, and HX848 were crossed with NC348. The crosses were made reciprocally to determine if the elite lines showed non-reciprocal fertility with these gene sources, or at least with the plants selected. The cross HX622 by NC344 was fully fertile either way the cross was made, and so this cross was dropped from the program. The other crosses were only fertile when the exotic source was used as the male parent.

Example 2

Backcrosses and Selection of Lines

The crosses LH185wx×NC346 and NC348 crossed with LH198wx, HX734, A68 and HX848 were planted in 1999 a winter nursery. Backcrosses were made from these $F_1$ crosses (used as male parents only) to their respective elite lines. The two $F_1$'s containing the waxy-starch gene were also self-pollinated. In addition reciprocal crosses were made between the F1's and two white genetic stock lines, Mo511W and Mo512W known to carry the GaS allele. At the same time each plant was cross pollinated, it was also self pollinated. In every case both of the ears of the reciprocal cross were fully fertile and varied for kernel quality and/or color. This confirmed that the North Carolina lines in fact did carry the GaS allele. In addition to these backcrosses and testcrosses, crosses were made between HX622 and Mo512W, again using Mo512W as a male parent.

These backcross populations of A681, HX734, HX844, and HX848 were planted in a nursery near Hooper, Nebr. in 2000. About 200 plants were used to represent each backcross population. Selections were made among the population of BC1 plants in each backcross population for plants showing the most similarity to its recurrent parent. Each of the selected plants were self pollinated, and then immediately pollinated with pollen from a homozygous purple pollen source. Then pollen from the plant was used to pollinate an ear of the recurrent elite inbred to produce the BC2 populations. In September, 2000 the ears of the best of the selected plants were harvested, along with their respective backcrosses. If any purple seeds occurred on the selected plant, it indicated that individual plant did not carry the GaS allele or that it lacked appropriate modifier genes, and both this plant (and its backcross) was discarded. Strong selection for complete absence of purple seeds was done.

The $F_2$ populations of LH198wx×NC348 and LH185wx×NC346 were sorted to obtain four sub-populations; white/waxy, white/nornal starch, yellow/waxy, and yellow/normal starch. Each of these sub-populations was treated separately for continued backcrossing. In the same manner as described above, the backcrosses were made to either the normal or waxy version of the elite line, so that four separate backcross populations were made for each elite line.

Also the $F_1$ HX622×Mo512W was planted in the summer 2000 nursery. It was crossed as a male to HX622. This $BC_1$ population was used to continue backcrossing to HX622.

During the winter, 2000–2001, each of these populations of elite lines was planted in a winter nursery on Molokai, Hi. The technique of self-pollinating plants and simultaneously pollinating the same ear with our purple marker is used. Then the pollen of the plant is used to pollinate an ear of the recurrent parent, producing $BC_3$ and $BC_2$ populations. In this way another backcross generation is accomplished of each population/sub-population of each elite line. The backcrosses were harvested in early March, 2001 and replanted as soon as practical on Molokai. Another cycle of backcrossing and selection is accomplished and ready for selection and harvest in July to produce the $BC_4$ and $BC_3$ populations. In July the breeding nursery is replanted on Molokai. Part of each $BC_4$ and $BC_3$ population are used to plant the nursery for still another cycle of backcross breeding. The rest of each sub-population is selected for trueness of phenotype to the recurrent parent, self pollinated and $BC_5$ and $BC_4$ populations as well as $BC_4S_1$ lines are harvested in November.

Selections are made among the $BC_4S_1$'s. Plants are pollinated immediately and cross-pollinated by the purple marker. One fourth of the ear-rows are homozygous for GaS, and in these rows none of the pollinated plants show any purple seeds. These homozygous rows are then increased, tested for agronomic performance, and crossed into hybrids during the summer. An increase of the best prospects was also made during the summer, 2001. The hybrids are then tested for performance in Chile during October, 2001 to March, 2002. The best of these are available for demonstration purposes in the U.S. during the following summer.

$BC_5$'s are then available to self and select for homozygosity. The $BC_5$'s are planted in the Molokai nursery in November. By March homozygous ear rows are selected. These $BC_5$'s are increased by selfing during the summer and then crossed into hybrids during the winter. These hybrids are available for testing and demonstration the following summer.

Example 3

Test for Genes Affecting Kernel Color and Quality

When the GaS system of the present invention is used in waxy endosperm hybrids (or any other recessive genes affecting kernel color or quality) a rapid test can be performed to any desired accuracy level. In the case of waxy endosperm, one can abrade the surface of the kernel and apply an iodine solution (e.g., medicinal tincture of iodine works well). The kernels with waxy starch will stain a reddish color, while kernels with the dominant normal starch will stain a blue-black. The presence of normal endosperm kernels in a waxy-starch GaS hybrid indicates mixtures of off-type and potentially GMO kernels in the corn sample. Sample sizes can be such that test accuracy is whatever the tester desires. It is a rapid, inexpensive and accurate quality control measure.

Example 4

Development of Elite GaS Inbreds

The GaS gene, along with GaS modifier alleles, has been inserted into the elite lines shown in Table 1 using the "backcrossing" technique. The lines were crossed with the exotic gene source, and the resulting progeny were crossed again with the elite parent. This process was repeated in subsequent generations until essentially the whole phenotype/genotype of the elite parent was recovered, however the progeny also contain the $Ga^s$ allele and the necessary modifier genes. With selection for the $Ga^s$ allele and for the elite line phenotype, greater than 98% of the elite genotype was recovered in 4 to 6 backcross generations. Then the lines were selfed to recover homozygous $Ga^sGa^s$ individuals.

Table 1 shows the results of an experiment in which partially converted elite lines containing the $Ga^s$ allele were: (1) pollinated with pollen from a homozygous purple-seeded inbred and, (2) self pollinated immediately afterward. The pollen from the purple-seeded inbred, if it fertilizes an embryo of normal yellow or white dent corn, results in a purple kernel being formed on the ear. In each case all kernels were yellow except for the A681ga control line shown on the last line of Table 1. The A681ga control line without the $Ga^s$ showed nearly half of the kernels were fertilized by the purple pollen.

TABLE 1

| Elite Line | # ears | # kernels | # purple kernels |
|---|---|---|---|
| HX844 Ga$^s$ BC | 12 | 4320 | 0 |
| HX737 Ga$^s$ BC | 12 | 3876 | 0 |
| HX848 Ga$^s$ BC | 10 | 4070 | 0 |
| LH198 Ga$^s$ BC | 18 | 4158 | 0 |
| LH198wx Ga$^s$ BC | 17 | 3661 | 0 |
| LH185 Ga$^s$ BC | 12 | 2352 | 0 |
| LH185wx Ga$^s$ BC | 14 | 2869 | 0 |
| HX681 Ga$^s$ BC | 10 | 3910 | 0 |
| A681ga (Control) | 4 | 1484 | 717 |

Example 5

Evaluation of Cross Pollination

In a related experiment, inbred HX848Ga$^s$ was pollinated with pollen from Mo512w (a white inbred line containing Ga$^s$). Other plants of HX848 were pollinated with pollen from LH185Ga$^s$ with standard H185 pollen. The results are shown below in Table 2.

TABLE 2

| | # ears | # kernels |
|---|---|---|
| HX848 Ga$^s$Ga$^s$ × LH185 Ga$^s$ | 4 | 793 |
| HX848 Ga$^s$Ga$^s$ × LH185 | 4 | 0 |
| HX848 Ga$^s$Ga$^s$ × Mo512W Ga$^s$Ga$^s$ | 4 | 715 |

It is clear that pollen from plants containing the standard allele of this locus will not fertilize ovules on GaS GaS plants. Since all known dent corn hybrids in the U.S. only carry the standard ga allele, the GaS system provides effective protection from GMO corn pollen. This has enabled the production of corn that is free of GMO contamination.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method of producing corn hybrid seed in a production field comprising:
   a) planting a female elite yellow corn inbred which is homozygous for the GaS allele;
   b) planting a male corn inbred line which is homozygous for the GaS allele, and
   c) allowing said male to cross with said female to produce $F_1$ hybrid seed which is homozygous for the GaS allele, and harvesting the resultant $F_1$ hybrid seed.

2. The method of claim 1 wherein said male corn inbred is an elite yellow corn inbred.

3. The $F_1$ seed produced by the method of claim 1.

4. A method of producing field corn comprising:
   a) planting a male non-popcorn, non-sweetcorn corn inbred which is homozygous for the GaS allele;

b) allowing said male inbred to cross with a second corn genotype as the female to produce $F_1$ hybrid seed and harvesting the resultant $F_1$ seed.

5. The method of claim 4 wherein said second corn genotype is an elite yellow corn inbred.

6. The F1 seed produced by the method of claim 4, wherein said F1 seed is an elite yellow F1 seed.

7. An elite yellow corn inbred plant homozygous for GaS alleles.

8. Yellow dent or flint corn seed produced by selfing the inbred plant of claim 7.

9. Elite yellow corn hybrid plants, which contain at least one GaS allele and which are not sweetcorn and not popcorn, produced by using the inbred plant of claim 7 as one of its parents.

10. An elite inbred corn plant heterozygous for GaS and ga alleles.

11. Corn seed produced by selfing the inbred plant of claim 10 wherein the seed contains at least one GaS allele.

12. Elite yellow corn hybrid plants, which contain at least one GaS allele and which are not sweetcorn, produced by using the inbred plant of claim 10 as one of its parent.

13. The method of claim 1 wherein said $F_1$ seed produced has less than 0.05 percent seed produced by contamination or pollination from nearby corn fields.

14. The method of claim 1 wherein said $F_1$ seed produced has less than 0.01 percent seed produced by contamination or pollination from nearby corn fields.

15. A method of producing field corn comprising:
 a) planting a male non-popcorn, non-sweetcorn elite yellow corn inbred which is homozygous for the GaS allele; and
 b) allowing said male inbred to cross with a second corn genotype as the female to produce $F_1$ hybrid seed and harvesting the resultant $F_1$ seed.

* * * * *